(12) United States Patent
Park et al.

(10) Patent No.: US 8,349,804 B2
(45) Date of Patent: Jan. 8, 2013

(54) BONE GRAFT AND SCAFFOLDING MATERIALS IMMOBILIZED WITH TYPE I COLLAGEN BINDING PEPTIDES

(75) Inventors: Yoon-Jeong Park, Seoul (KR); Chong-Pyoung Chung, Songpa-gu (KR); Seung-Jin Lee, Seoul (KR); Jue-Yeon Lee, Gyeonggi-do (KR)

(73) Assignee: Seoul National University Industry Foundation, Seoul (KR)

( * ) Notice: Subject to any disclaimer, the term of this patent is extended or adjusted under 35 U.S.C. 154(b) by 793 days.

(21) Appl. No.: 12/278,009

(22) PCT Filed: Jan. 19, 2007

(86) PCT No.: PCT/KR2007/000335
§ 371 (c)(1),
(2), (4) Date: Jun. 10, 2009

(87) PCT Pub. No.: WO2007/089084
PCT Pub. Date: Aug. 9, 2007

(65) Prior Publication Data
US 2011/0045048 A1  Feb. 24, 2011

(30) Foreign Application Priority Data
Feb. 3, 2006  (KR) .................... 10-2006-0010712

(51) Int. Cl.
*A61K 38/10* (2006.01)
*A61K 38/16* (2006.01)

(52) U.S. Cl. ............... 514/21.4; 514/21.5; 514/21.7; 514/21.9; 530/326; 530/327; 530/328

(58) Field of Classification Search .......... None
See application file for complete search history.

(56) References Cited

U.S. PATENT DOCUMENTS
5,211,661 A  5/1993  Shinjou et al.
6,509,026 B1 *  1/2003  Ashkar et al. ............... 424/422
6,818,621 B2 *  11/2004  Ashkar .......................... 514/9.4

FOREIGN PATENT DOCUMENTS
KR  1001055110000     10/1996
KR  1020020075605 A   10/2002
WO  WO2005/089826  *  9/2005

OTHER PUBLICATIONS

Nasu et al. "Expression of wild-type and mutated rabbit osteopontin in *Escherichia coli*, and their effects on adhesion and migration of P388D1 cells." Biochem. J. (1995) 307, 257-265.*
Camelo, M., et al., Periodontal regeneration with an autogenous bone-Bio-Oss composite graft and a Bio-Gide membrane, International J. Periodontics Restorative Dent., 2001, 21 (2), 109-119, abstract only.

* cited by examiner

*Primary Examiner* — Anish Gupta
(74) *Attorney, Agent, or Firm* — Andrew D. Gerschutz; Tristan A. Fuierer; Moore & Van Allen, PLLC

(57) ABSTRACT

The present invention relates to a pharmaceutical composition comprising a bone graft material, a scaffold for tissue engineering applications and type I collagen Binding Peptides which have bone calcification-promoting peptides immobilized on the surface, and more particularly, to a bone graft material and a scaffold for tissue engineering applications (hereinafter, referred to as scaffold), which have peptides specifically binding with type I collagen immobilized on the surface, and pharmaceutical composition for recovering tissue regeneration containing type I collagen binding-inducing peptide. In the inventive bone graft material and scaffold for tissue engineering applications, the cells related to regeneration by collagen binding-inducing peptide adhered to the surface, promote an adhesion of type I collagen binding-inducing peptide (main ingredients of extracellular matrix) to increase differentiation rate into bone tissues, and promote a calcification which is last step of bone regeneration to maximize a tissue regeneration finally.

18 Claims, 4 Drawing Sheets

(a)  (b)
(c)  (d)

```
                         SEQUENCE LISTING

<160> NUMBER OF SEQ ID NOS: 6

<210> SEQ ID NO 1
<211> LENGTH: 8
<212> TYPE: PRT
<213> ORGANISM: Oryctolagus cuniculus

<400> SEQUENCE: 1

Tyr Arg Leu Lys Arg Ser Lys Ser
1               5

<210> SEQ ID NO 2
<211> LENGTH: 13
<212> TYPE: PRT
<213> ORGANISM: Oryctolagus cuniculus

<400> SEQUENCE: 2

Lys Met Phe His Val Ser Asn Ala Gln Tyr Pro Gly Ala
1               5                   10

<210> SEQ ID NO 3
<211> LENGTH: 21
<212> TYPE: PRT
<213> ORGANISM: Oryctolagus cuniculus

<400> SEQUENCE: 3

Tyr Arg Leu Lys Arg Ser Lys Ser Lys Met Phe His Val Ser Asn Ala
1               5                   10                  15

Gln Tyr Pro Gly Ala
            20

<210> SEQ ID NO 4
<211> LENGTH: 7
<212> TYPE: PRT
<213> ORGANISM: Homo sapiens

<400> SEQUENCE: 4

Tyr Gly Leu Arg Ser Lys Ser
1               5

<210> SEQ ID NO 5
<211> LENGTH: 14
<212> TYPE: PRT
<213> ORGANISM: Homo sapiens

<400> SEQUENCE: 5

Lys Lys Phe Arg Arg Pro Asp Ile Gln Tyr Pro Asp Ala Thr
1               5                   10

<210> SEQ ID NO 6
<211> LENGTH: 21
<212> TYPE: PRT
<213> ORGANISM: Homo sapiens

<400> SEQUENCE: 6

Tyr Gly Leu Arg Ser Lys Ser Lys Lys Phe Arg Arg Pro Asp Ile Gln
1               5                   10                  15

Tyr Pro Asp Ala Thr
            20
```

BONE GRAFT AND SCAFFOLDING MATERIALS IMMOBILIZED WITH TYPE I COLLAGEN BINDING PEPTIDES

CROSS-REFERENCE TO RELATED APPLICATIONS

This application is filed under the provisions of 35 U.S.C. §371 and claims the priority of International Patent Application No. PCT/KR2007/000335 filed on 19 Jan. 2007 entitled "Bone Graft and Scaffolding Materials Immobilized with Type I Collagen Binding Peptides" in the name of Yoon-Jeong Park, et al., which claims priority of Korean Patent Application No. 10-2006-0010712 filed on 3 Feb. 2006, both of which are hereby incorporated by reference herein in their entirety.

TECHNICAL FIELD

The present invention relates to a bone graft material and a scaffold for tissue engineering applications, which have bone calcification-promoting peptides immobilized on the surface thereof and a pharmaceutical composition comprising a peptide inducing type I collagen binding, and more particularly, to a bone graft material and a scaffold for tissue engineering applications (hereinafter, referred to as scaffold), which have peptides specifically binding to type I collagen immobilized on the surface thereof, and a pharmaceutical composition for promoting tissue regeneration containing type I collagen binding-inducing peptide.

BACKGROUND ART

Periodontal tissue that supports teeth consists generally of the alveolar bone, the periodontal ligament tissue forming the periodontal membrane between the alveolar bone and the teeth, and the connective tissue. The loss of alveolar bone caused by the progression of periodontitis involves the loss of periodontal ligament tissue, and at sites of the loss of periodontal ligament tissue, the normal repair of alveolar bone and periodontal ligament tissue after the treatment of periodontitis becomes impossible due to excessive growth of connective tissue. Also, even when new bone is formed, the periodontal ligament tissue will not be normally differentiated so that the loss of tooth function can be caused.

To solve such problems, an attempt to induce the complete regeneration or new formation of tissue using an artificial barrier membrane together with autografting in guided periodontal regeneration is actively made. Also, for the regeneration of bone tissue, a tissue engineering scaffold is used as a bone graft material. Since cases showing the effective induction of periodontal tissue and bone tissue by the introduction of bone graft materials and scaffolds (Camelo, M. et al., International J. Periodont. Restorative Dent. 21:109, 2001) were reported for recent ten years, various materials, including bone powder particles made of bovine bone, have been used as bone materials and tissue engineering scaffolds for tissue regeneration.

Meanwhile, in order to improve the efficiency of such bone graft materials and scaffolds for tissue regeneration, studies to attach materials capable of improving tissue regeneration to the bone graft materials and the scaffolds are now conducted. Firstly, protein ingredients of extracellular matrices are adhered to the surface of bone graft materials and scaffolds, then calcification is performed to finally form bone tissues. Herein, if collagen, main ingredients of extracellular matrices is induced, early reaction of bone tissue regeneration is rapidly induced to result in increasing the regeneration rate. Furthermore, such extracellular matrices is reported to be excellent in the ability of the repair and regeneration of damaged tissue, and their excellent ability to regenerate tissue was also shown in the results of actual clinical tests.

Such examples include artificial biocompatible material comprising a porous sintered body of calcium phosphate and collagen derivatives as mucosal adjuvants (Korean Patent Registration 105511) an artificial bone material for replacing natural bone which promotes osteoblast adhesion (KRP 487693), collagen scaffold for bone regeneration (Korean Patent Registration 1427557), etc.

However, collagen, the most materials consisting of extracellular matrix is high-molecular-weight proteins having several tens of kDa, and it is extracted directly from biological tissues or prepared as a recombinant protein, and thus being relatively expensive and thermally unstable, therefore it is difficult to prepare various pharmaceutical compositions.

Accordingly, the present inventors have made extensive efforts to solve the above-described problems occurring in the prior art, and consequently found that the rate of bone tissue regeneration is increased by fixing the peptides capable of inducing rapid adhesion of collagen (main ingredient of extracellular matrix) on the surface of bone graft materials and scaffolds, furthermore, the risk of immune reaction is low in its application to the body because of small molecular weights thereof, and the effect of drugs lasts because of its stable existence in the body as well. On the basis of these findings, the present invention has been completed.

SUMMARY OF THE INVENTION

An object of the present invention is to provide with a bone graft material for promoting bone tissue regeneration and a scaffold for tissue engineering applications, which have a peptide inducing type I collagen binding immobilized on the surface thereof.

Another object of the present invention is to provide a pharmaceutical composition for promoting tissue regeneration, which contains a peptide inducing collagen.

To achieve the above objects, the present invention provides a bone graft material and a scaffold for tissue engineering applications, which have a peptide inducing type I collagen binding immobilized on the surface thereof.

In one aspect, the present invention provides a pharmaceutical composition for promoting tissue regeneration, which contains a peptide inducing type I collagen binding.

In the present invention, preferably, a peptide inducing type I collagen binding essentially comprises any one amino acid sequence among SEQ ID NO: 1 to SEQ ID NO: 6, and more preferably, the peptide has an addition of cysteine at N-terminal end of amino acid sequence selected from SEQ ID NO: 1 to SEQ ID NO: 6.

Another features and embodiments of the present invention will be more clarified from the following "detailed description" and the appended "claims".

BRIEF DESCRIPTION OF DRAWINGS

In FIG. 2, (a) shows the adhesion pattern of cells to the surface non-covered with peptides, and (b) (c) and (d) show the adhesion patterns of cells on bone graft surfaces with immobilized peptides derived from bone sialoprotein 1 (BSP 1) of *Oryctolagus cuniculus*, respectively.

In FIG. 3, (a) is non-treatment group with peptides, and (b) (c) and (d) show aspects of cell calcification on bone graft surfaces immobilized with peptides derived from bone sialoprotein 1 (BSP 1) of *Oryctolagus cuniculus*, respectively.

DETAILED DESCRIPTION OF THE INVENTION, AND PREFERRED EMBODIMENTS

Figure 1:
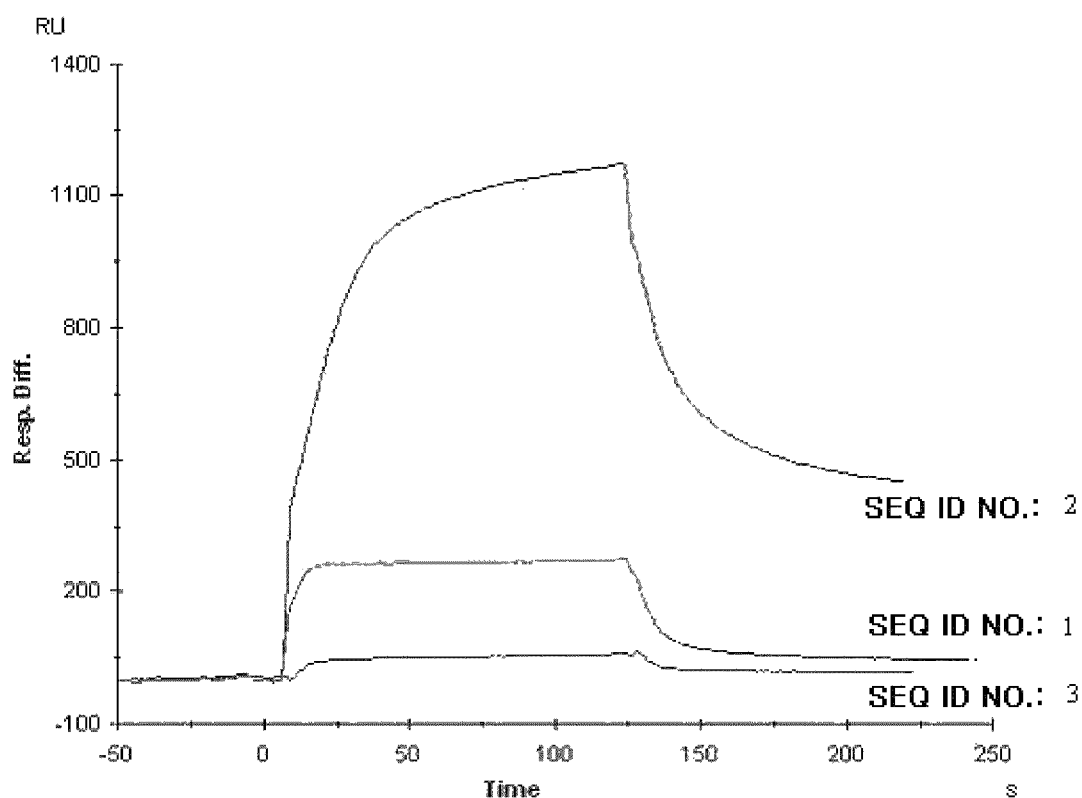
FIG. 1 shows the analysis of adhesion degree between collagen and the peptides according to the present invention.

In one aspect, the present invention relates to a bone graft material for promoting bone tissue regeneration and a scaffold for tissue engineering applications, which have a peptide inducing type I collagen binding immobilized on the surface thereof. In other words, the present invention relates to a bone graft material and a scaffold for tissue regeneration, on the surfaces of which a peptide inducing collagen binding is immobilized so that the bone graft material and the scaffold have pharmacological activity, whereby their efficiency in the regeneration of bone tissue or other tissues can be improved.

Preferably, a peptide inducing type I collagen binding may essentially comprise any one amino acid sequence among SEQ ID NO: 1 to SEQ ID NO: 6. In the present invention, a peptide essentially comprising a specific amino acid sequence includes peptides having a similar function, in which another amino acid sequence is added to the amino acid sequence of the present invention. Furthermore, the peptide includes peptides having an addition of cysteine at the N-terminal end of the amino acid sequence, as well as peptides having an addition of other amino group. For example, there is a peptide in which cysteine is linked at the N-terminal end of amino acid sequence selected from SEQ ID NO: 1 to SEQ ID NO: 6, via a spacer consisting of two glycines (CGG- and CGGGGG-) in order to facilitate to immobilize to a bone graft material or a scaffold chemically.

In the present invention, all kinds and types of bone graft materials and polymer scaffolds can be used if they are used in the technical field. Preferred examples of these bone graft materials include organism-derived bone mineral powders and porous blocks originated from autogeneous bone such as bovine bone and porcine bone etc., synthetic hydroxyapatite powder and porous blocks thereof, tricalcium phosphate powders and porous blocks thereof, monocalcium phosphate powder and porous blocks, bone graft materials containing silicon dioxide (silica) as a main ingredient, bone-packing graft materials containing a mixture of silica and polymer as a main ingredient, chitosan, fine particles containing biocompatible polymers as a main ingredient, and titanium and the like.

Moreover, examples of polymer scaffolds include chitosan, porous scaffolds containing biocompatible polymers as a main ingredient and three-dimensional porous scaffolds of titanium. Herein, the surface of bone graft materials and scaffolds is preferably modified to facilitate binding of active peptides.

The peptide inducing collagen binding according to the present invention promotes binding of collagen which is a main ingredient of extracellular matrix in primary differentiation of osteoblast, whereby promoting a calcification, the last step of differentiation. Thus, the peptide inducing collagen binding has suitable characteristics for the regeneration of bone tissue and periodontal tissue.

The peptide inducing collagen binding according to the present invention has free amino group or cysteine at the N-terminal end and thus easy to immobilize on the surface of bone graft materials and scaffolds by crosslinkers. Crosslinkers suitable for use in the present invention include, but are not limited to, 1,4-bis-maleimidobutane (BMB), 1,11-bis-maleimido tetraethyleneglycol (BM[PEO]$_4$), 1-ethyl-3-[3-dimethyl aminopropyl]carbodiimide hydrochloride (EDC), succinimidyl-4-[N-maleimido methylcyclohexane-1-carboxy-[6-amidocaproate]] (SMCC) and sulfo-SMCC, succimidyl 6-[3-(2-pyridyldithio)-ropionamido]hexanoate] (SPDP) and sulfo-SPDP, m-maleimidobenzoyl-N-hydroxysuccinimide ester (MBS) and sulfo-MBS, succimidyl[4-(p-maleimidophenyl) butyrate] (SMPB) and sulfo-SMPB.

In another aspect, the present invention relates to a pharmaceutical composition for promoting tissue regeneration, wherein a peptide inducing collagen binding is embedded in the pharmaceutical composition for promoting tissue regeneration to have pharmacological activity, whereby their efficiency in the regeneration of bone tissue or other tissues can be improved.

In the present pharmaceutical composition for promoting tissue regeneration, all kinds and types of pharmaceutical formulation can be used if they are used in the technical field, specifically, ointment type or cream type that can be applied to skin is preferred. For the ointment or cream, general carriers such as fat, fatty oil, lanolin, vaseline, paraffin, lead, resin, plastic, glycols, higher alcohol, glycerin, water, emulsifier, suspension agent or proper additives can be utilized.

Additionally, the pharmaceutical composition may be used in the form of a gel, and general carriers such as chitosan, alginate, prophylene glycol, prophylene glycol alginate, poloxamer, chondroitin sulfate and the like can preferably be used as the gel Hereinafter, the present invention will be described in further detail about a bone graft material and a scaffold for tissue engineering applications, which have the invention a peptide inducing type I collagen binding immobilized thereon, and a pharmaceutical composition containing a peptide inducing type I collagen binding according to the present invention The peptide inducing collagen binding used in the present invention is obtained by isolating and extracting active site amino acid sequence from protein constituting the extracellular matrix and then subjected to chemical modification so as to maintain its active structure.

Specifically, the peptide inducing collagen binding essentially contains any one amino acid sequence among amino acid sequences at position 85-105 of bone sialoprotein 1 (BSP 1) of *Oryctolagus cuniculus*: YRLKRSKS (SEQ ID NO: 1), KMFHVSNAQYPGA (SEQ ID NO: 2), YRLKRSKSKMF-HVSNAQYPGA (SEQ ID NO: 3); and amino acid sequences at position 149-169 of bone sialoprotein I of human: YGLR-SKS (SEQ ID NO: 4), KKFRRPDIQYPDAT (SEQ ID NO: 5), YGLRSKSKKFRRPDIQYPDAT (SEQ ID NO: 6).

In the process of chemical modification for stabilizing peptide structure, a cysteine is added to the N-terminal end of amino acid sequence selected from the amino acid sequences in the form of CGG or CGGGGG spacer, and synthesized chemically to prepare a peptide.

The modification process of the surface of a bone graft material and a polymer scaffold is performed in order to bind the peptide prepared above to the surface thereof. Herein, the used bone graft material and polymer scaffold is any one selected from the group consisting of organism-derived bone mineral powders and porous blocks originated from autogeneous bone, bovine bone and porcine bone, synthetic hydroxyapatite powders and porous blocks thereof, tricalcium phosphate powders and porous blocks thereof, monocalcium phosphate powders and porous blocks thereof, bone graft materials containing silicon dioxide (silica) as a main ingredient, bone-packing graft materials containing a mixture of silica and polymer as a main ingredient, chitosan, fine particles containing biocompatible polymers as main ingredient and porous scaffolds thereof, titanium and three-dimensional scaffolds thereof etc., and the modification process may be little different depending on its kinds.

The modification process of surface is performed by removing the impurities on the surface of a bone graft material and a polymer scaffold, and then adding a crosslinker to bind the peptides to the surface chemically. Herein, a functional group capable of binding with cysteine located at the end of peptide, for example, a —SH group is introduced in the surface or the surface is treated to form an amine ($NH_2$), thereby achieving efficient cross-linking by cosslinker.

Particles of a bone graft material or a scaffold bonded with crosslinker are allowed to react with the peptide prepared above, and then washed to obtain the bone graft material and the scaffold having the peptides immobilized. The peptides are chemically bound to the surface of bone graft materials and scaffolds so that they are immobilized on the surface in an amount of preferably 0.1-10 $mg/cm^2$. More preferably, the peptides consist of 5-30 amino acids and are immobilized on the surface in an amount of 1-5 $mg/cm^2$.

In addition, the peptides are sealed to prepare a pharmaceutical composition for promoting tissue regeneration, wherein the composition is prepared in a form of a liquid, a gel, ointment, or cream. Especially, the ointment or cream is prepared by evenly mixing the peptide with carriers such as fat, fatty oil, lanolin, vaseline, paraffin, lead, resin, plastic, glycols, higher alcohol, glycerin, water, emulsifier, suspension agent and proper additives, which are generally used in preparing ointment or cream in the art.

EXAMPLES

Hereinafter, the present invention will be described in further detail by examples. It will however be obvious to a person skilled in the art that these examples are provided for illustrative purpose only and are not construed to limit the scope of the present invention.

Especially, the following examples illustrate only peptides inducing collagen binding of SEQ ID NO: 1 to 3, but it will be obvious to a person skilled in the art that the similar effect could be obtained when peptides inducing collagen binding of amino acid sequences at position 149-169 of bone sialoprotein I of human: YGLRSKS (SEQ ID NO: 4), KKFRRP-DIQYPDAT (SEQ ID NO: 5), YGLRSKSKKFRRPDIQYP-DAT (SEQ ID NO: 6) are synthesized and cysteine and the like is added to the end thereof.

Example 1

Synthesis of Peptide Containing the Type I Collagen-Binding Active Domain

Cysteine was linked at each N-terminal end of peptides having amino acid sequences of SEQ ID NO: 1. 2 and 3 comprising a type I collagen-binding active domain of Bone sialoprotein 1 (BSP 1) of *Oryctolagus cuniculus* via a spacer (GGG-, and CGGGGG), thus synthesizing a peptide inducing type I collagen binding.

Figure 4:
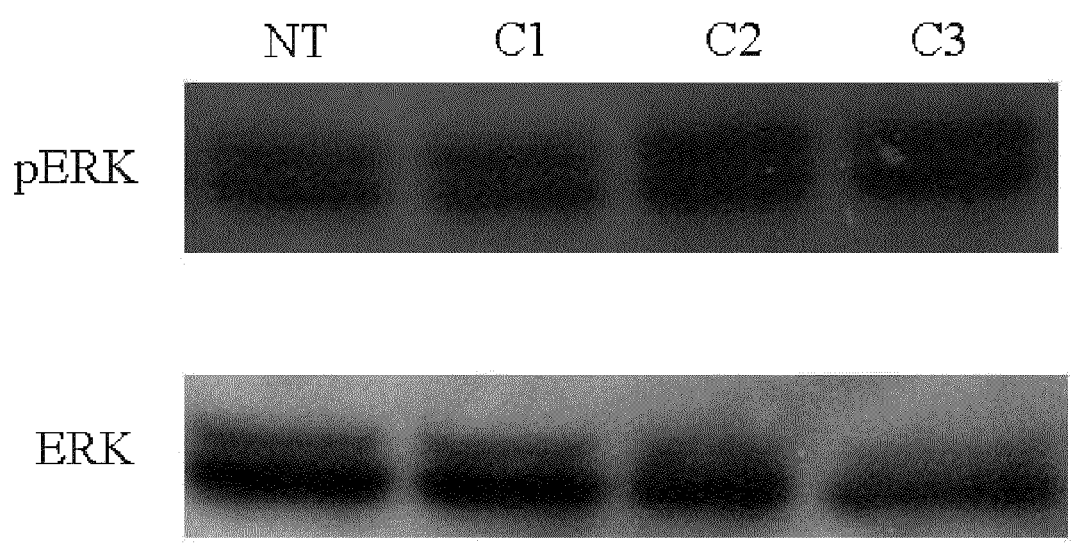
FIG. 4 is photographs showing the results of Western blot for the amount of intracellular signal transfer marker ERK in cells collected after exposing the inventive peptides to the cultured cells for given times (NT: cells non-treated with peptides; C1: cells treated with peptides of SEQ ID NO: 1; C2: cells treated with peptides of SEQ ID NO: 2; C3: cells treated with peptides of SEQ ID NO: 3).

The synthesized peptide's affinity to type I collagen was examined using Biacore X (Biacore Co., Sweden). After the type I collagen was bound to CM5 chip, the amount of peptides binding with collagen was quantitated while flowing the prepared peptide dissolved to be 4 μmol into micro-channels of Biacore X (FIG. 1). As a result, as shown in FIG. 4, the peptide of SEQ ID NO: 3 showed the highest affinity to collagen, and the peptide of SEQ ID NO: 2 showed the lowest affinity to collagen.

Example 2

Immobilization of Peptide Inducing Type I Collagen Binding on Bovine Bone-Derived Bone Mineral Particles Bovine bone-derived bone mineral particles were washed with ethanol under reduced pressure and then left to stand in a vacuum oven at 100° C. for 20 hours so as to remove impurities from the surface. The surface of the bone mineral particles was treated with a solution of 3-aminopropyl ethoxysilane (APTES) dissolved in hexane, followed by washing. This resulted in the formation of amine residues on the surface, to which crosslinker BMB was then added and bound. Bone mineral particles bonded with crosslinker were allowed to react with each peptide synthesized in example 1 for 12 hours, followed by washing, thus yielding the bone mineral particles having the peptides immobilized on the surface thereof.

Example 3

Immobilization of Peptide Inducing Type I Collagen Binding on Synthetic Hydroxyapatite and Tricalcium Phosphate Bone graft powders of synthetic hydroxyapatite and tricalcium phosphate were washed with ethanol under reduced pressure and then left to stand in a vacuum oven at 100° C. for 20 hours so as to remove impurities from the surface. The surface of the bone mineral particles was treated with a solution of 3-aminopropyl ethoxysilane (APTES) in hexane, followed by washing. This resulted in the formation of amine residues on the surface, to which crosslinker BMB was then added and bound. The bone mineral particles with the bound crosslinker were allowed to react with each peptide synthesized in example 1 for 12 hours, followed by washing, thus yielding the bone mineral particles having the peptides immobilized on the surface thereof.

Example 4

Immobilization of Peptide Inducing Type I Collagen Binding on Bone Graft Material with Chitosan A bone graft material with chitosan prepared in the form of a powdery or porous scaffold was added to 2 ml of phosphate buffer (pH 7.4) to hydrate the surface. To this solution, sulfo-SMCC as a crosslinker was added at a concentration of 5 mg/ml, and the mixture was stirred for 2 hours to introduce functional groups on the surface of the bone graft material with chitosan. After 2 hours of reaction at ambient temperature, the bone graft material with chitosan was washed and allowed to react with each solution of 10 mg of each peptide synthesized in example 1, dissolved in each 100 μl of phosphate buffer for 24 hours, followed by washing, thus yielding the bone graft material with chitosan having the peptide immobilized thereon.

Example 5

Immobilization of Peptide Inducing Type I Collagen Binding on Bone Graft Material with Polylactic Acid A bone grafting powder or porous scaffold of polylactic acid was added to phosphate buffer (pH 4.7) to hydrate the surface, followed by reaction with 20 mg/ml of cystamine hydrochloride solution. To this solution, EDC was added dropwise to activate the carboxylic acid on the surface of the bone graft material. The mixture was reacted for 24 hours, washed, and allowed to react with 1 ml of dithiothreniol (DTT) solution (30 mg/ml) for 24 hours so as to introduce sulfhydryl groups onto the surface of the polylactic acid. The modified polylactic acid bone graft material was mixed with each peptide synthesized in example 1 so as to immobilize by S—S bonds between the sulfhydryl groups of the bone grafting material and the peptides.

Example 6

Test of Cell Adhesion of Peptides According to the Present Invention

Human-osteocarcoma cells (KCLB No. 21543) were inoculated on the surface of bone graft materials prepared in Examples 2 and then cultured for 2 hours. The bone graft materials with the cultured human-osteocarcoma cell were fixed with 2% glutaraldehyde solution. The fixed bone graft materials were treated with 1% triton X-100 and then added with a fluorescent-labeled phalloidin solution, thus staining the attached cytoplasm. Then, after the samples were washed and fixed, the cells adhered to the bone graft materials were observed with a confocal laser scanning microscope (FIG. 2).

Figure 2:
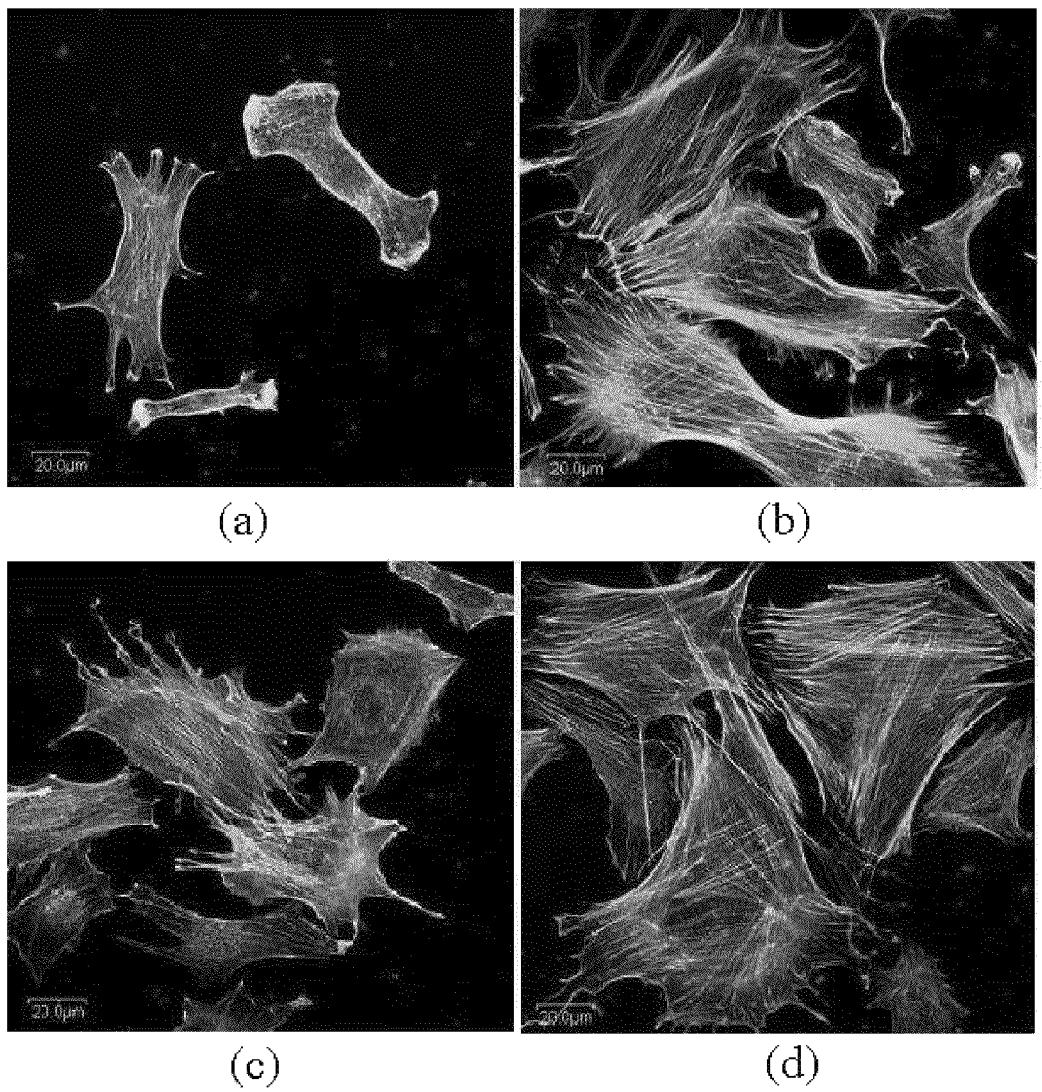
FIG. 2 shows confocal laser scanning microscopic images showing the cell adhesion patterns of the inventive peptides.

In FIG. 2, (a) shows the cell adhesion on the surface coated with BSA (Bovine serum albumin), and (b), (c) and (d) show the cell adhesions on the surfaces coated with peptides in which cysteine was added at each N-terminal end of amino acid sequences of SEQ ID NO: 1, 2 and 3, respectively. As a result, for the surface coated with BSA, spherical and unstable adhesion aspect of the cells was observed, whereas on the surfaces coated with the peptides inducing collagen binding, the stable adhesion of the cells (including the elongation of the cytoplasm in most of the cells after 3 hours of the cell culture) was observed.

Example 7

Test of Calcification by Peptides According to the Present Invention

The bone graft materials prepared in Examples 2 was added to a medium for forming a hard tissue containing calcein (fluorescent marker of calcium), and human mesenchymally derived stem cells ($C_2Cl_2$: ATCC CRL-1772) were cultured for 14 days. The cultured osteoblasts werefixed with 2% glutaraldehyde solution and treated with 1% triton X-100 and then added with a fluorescent-labeled phalloidin solution, thus staining the fixed cytoplasm. Then, after the samples were washed and fixed, the calcium adhered to extracellular matrix was observed with a confocal laser scanning microscope (FIG. 3), on the surface of the bone graft materials.

Figure 3:
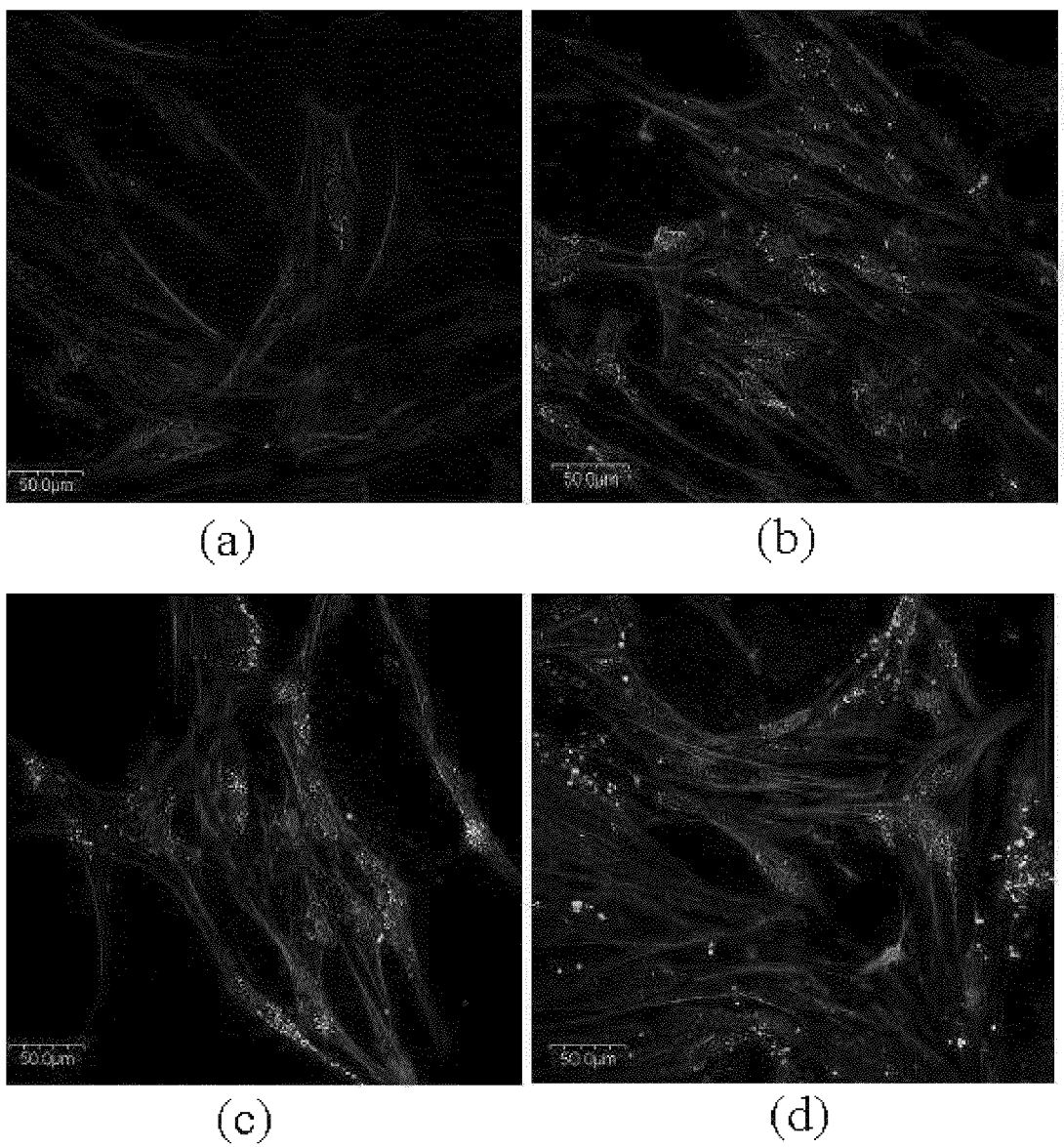
FIG. 3 is confocal laser scanning microscopic images showing an adhesion degree of calcium stained with calcein after culturing the inventive peptides in a medium for forming a hard tissue for given periods, which added with broth of the inventive peptides.

In FIG. 3, (a) shows the group without peptides of the present invention, and (b), (c) and (d) show the calcium adhesions within cells by peptides in which cysteine was added at each N-terminal end of amino acid sequences of SEQ ID NO: 1, 2 and 3, respectively. As a result, the groups with peptide inducing collagen binding, showed much more fluorescence than (a) group without the peptides, so it could be confirmed that the peptides inducing collagen binding promote a calcification of cells.

Example 8

Expression of Differentiation Marker Proteins in Osteoblasts Cultured on Surface of Peptide-Immobilized Bone Graft Material According to the Present Invention In order to examine the expression of differentiation marker protein in osteoblasts cultured on the surface of the bone graft material on which peptides added with cysteine at each N-terminal end of amino acid sequences of SEQ ID NOs: 1, 2 and 3, prepared in example 2 according to the present invention were immobilized, the peptides were exposed to human mesenchymally derived stem cells (C2C12) for 30 min, and collected to measure the amount of ERK protein, a marker proteins involved in intracellular signal transfer, by Western blot.

The human mesenchymally derived stem cells were transplanted to 60 mm of petridish, treated with peptides for 30 min. Whole intracellular protein was extracted and quantitated by Bradford method. 40☐ of protein was electrophoresed on acrylamide gel and transferred to nitrocellulose membrane, and ERK, intracellular signal transmission protein within cell was reacted with the antibody of phosphorylated ERK (pERK), followed by reacting with the second antibody labeled with a marker. The membrane was developed to observe the protein bands and measure densities thereof (FIG. 4).

As a result, as shown in FIG. 4, the expression of the phosphorylated ERK (pERK) in the cells treated with the peptides (C1, C2, C3) was significantly increased as compared to the case of the cells non-treated with the peptides (NT). This suggests that the differentiation into bone tissue of the cells grown on the surface of the bone graft material immobilizing the peptides inducing collagen binding was promoted.

INDUSTRIAL APPLICABILITY

As described and proved above in detail, the present invention provides the bone graft material and scaffold for tissue engineering applications having a surface immobilized with collagen binding-inducing peptide, capable of have suitable effect of tissue regeneration with small and low-concentrated dose. In the inventive bone graft material and scaffold for tissue engineering applications, the cells related to regeneration by collagen binding-inducing peptide adhered to the surface, promote an adhesion of type I collagen binding-inducing peptide (main ingredients of extracellular matrix) to increase differentiation rate into bone tissues, and promote a calcification which is last step of bone regeneration to maximize a tissue regeneration finally. Additionally, the risk of immune reaction is low in application to the body because of small molecular weights thereof, and the effect of drugs is lasted because of existing stably in the body as well, thus having an excellent convenience in case of regeneration operations of periodontal tissues, alveolar bones and other bone tissues.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A bone graft material comprising a peptide inducing type I collagen binding immobilized on a surface of the bone graft material, wherein the peptide comprises any one amino acid sequence selected from the group consisting of SEQ ID NO: 1, SEQ ID NO: 2, and SEQ ID NO: 3.

2. The bone graft material according to claim 1, wherein the peptide inducing type I collagen binding has an addition of cysteine at N-terminal end of the amino acid sequence selected from SEQ ID NO: 1 to 3.

3. The bone graft material according to claim 2, wherein said cysteine is added as CGG or CGGGGG spacer type.

4. The bone graft material according to claim 1, wherein the bone graft material is any one selected from the group consisting of organism-derived bone mineral powders and porous blocks originated from autogeneous bone, bovine bone and porcine bone, synthetic hydroxyapatite powders and porous blocks, tricalcium phosphate powders and porous blocks, monocalcium phosphate powders and porous blocks, bone graft materials containing silicon dioxide (silica) as main ingredient, bone-packing graft materials containing a mixture of silica and polymer as main ingredient, chitosan, fine particles containing biocompatible polymers as main ingredient, and titanium.

5. The bone graft material according to claim 1, wherein the peptide inducing type I collagen binding is immobilized by a crosslinker.

6. The bone graft material according to claim 5, wherein the crosslinker is any one or more selected from the group consisting of 1,4-bis-maleimidobutane (BMB), 1,11-bis-maleimido tetraethyleneglycol (BM[PEO]$_4$), 1-ethyl-3-[3-dimethyl aminopropyl]carbodiimide hydrochloride (EDC), succinimidyl-4-[N-maleimido methylcyclohexane-1-carboxy-[6-amidocaproate]] (SMCC) and sulfo-SMCC, succinimidyl 6-[3-(2-pyridyldithio)-ropionamido]hexanoate] (SPDP) and sulfo-SPDP), m-maleimidobenzoyl-N-hydroxysuccinimide ester (MBS) and sulfo-MBS, succimidyl[4-(p-maleimidophenyl) butyrate] (SMPB) and sulfo-SMPB.

7. A scaffold for tissue engineering applications comprising a peptide inducing type I collagen binding immobilized on a surface of the scaffold, wherein the peptide comprises any one amino acid sequence selected from the group consisting of SEQ ID NO: 1, SEQ ID NO: 2, and SEQ ID NO: 3.

8. The scaffold for tissue engineering applications according to claim 7, wherein the peptide inducing type I collagen binding has an addition of cysteine at N-terminal end of the amino acid sequence selected from SEQ ID NO: 1 to 3.

9. The scaffold for tissue engineering applications according to claim 8, wherein said cysteine is added as CGG or CGGGGG spacer type.

10. The scaffold for tissue engineering applications according to claim 7, wherein the scaffold for tissue engineering applications is any one or more selected from the group consisting of chitosan, porous scaffolds containing biocompatible polymers as main ingredient and three-dimensional scaffolds of titanium.

11. The scaffold for tissue engineering applications according to claim 7, wherein the peptide inducing type I collagen binding is immobilized by a crosslinker.

12. The scaffold for tissue engineering applications according to claim 11, wherein the crosslinker is any one or more selected from the group consisting of 1,4-bis-maleimidobutane (BMB), 1,11-bis-maleimido tetraethyleneglycol (BM[PEO]$_4$), 1-ethyl-3-[3-dimethyl aminopropyl]carbodiimide hydrochloride (EDC), succinimidyl-4-[N-maleimido methylcyclohexane-1-carboxy-[6-amidocaproate]] (SMCC) and sulfo-SMCC, succinimidyl 6-[3-(2-pyridyldithio)-ropionamido]hexanoate] (SPDP) and sulfo-SPDP), m-maleimidobenzoyl-N-hydroxysuccinimide ester (MBS) and sulfo-MBS, succinimidyl[4-(p-maleimidophenyl) butyrate] (SMPB) and sulfo-SMPB.

13. A bone graft material comprising a peptide inducing type I collagen binding immobilized on a surface of the bone graft material, wherein the peptide has the sequence consisting of SEQ ID NO:5 or SEQ ID NO:6.

14. A bone graft material according to claim 13, wherein the peptide inducing type I collagen binding has an addition of cysteine at the N-terminal end of the amino acid sequence consisting of SEQ ID NO:5 or SEQ ID NO:6.

15. The bone graft material according to claim 14, wherein said cysteine is added as CGG or CGGGGG spacer type.

16. The bone graft material according to claim 13, wherein the bone graft material is any one selected from the group consisting of organism-derived bone mineral powders and porous blocks originated from autogeneous bone, bovine bone and porcine bone, synthetic hydroxyapatite powders and porous blocks, tricalcium phosphate powders and porous blocks, monocalcium phosphate powders and porous blocks, bone graft materials containing silicon dioxide (silica) as main ingredient, bone-packing graft materials containing a mixture of silica and polymer as main ingredient, chitosan, fine particles containing biocompatible polymers as main ingredient, and titanium.

17. The bone graft material according to claim 13, wherein the peptide inducing type I collagen binding is immobilized by a crosslinker.

18. The bone graft material according to claim 17, wherein the crosslinker is any one or more selected from the group consisting of 1,4-bis-maleimidobutane (BMB), 1,11-bis-maleimido tetraethyleneglycol (BM[PEO]$_4$), 1-ethyl-3-[3-dimethyl aminopropyl]carbodiimide hydrochloride (EDC), succinimidyl-4-[N-maleimido methylcyclohexane-1-carboxy-[6-amidocaproate]] (SMCC) and sulfo-SMCC, succinimidyl 6-[3-(2-pyridyldithio)-ropionamido]hexanoate] (SPDP) and sulfo-SPDP), m-maleimidobenzoyl-N-hydroxysuccinimide ester (MBS) and sulfo-MBS, succimidyl[4-(p-maleimidophenyl) butyrate] (SMPB) and sulfo-SMPB.

* * * * *